(12) United States Patent
Nakagawa (10) Patent No.: US 9,501,846 B2
(45) Date of Patent: Nov. 22, 2016

(54) IMAGE PROCESSING DEVICE, IMAGE PROCESSING METHOD, IMAGE PROCESSING PROGRAM, AND RECORDING MEDIUM STORING SAID PROGRAM FOR PRODUCING NOISE-ELIMINATED IMAGE

(71) Applicant: KOWA COMPANY, LTD., Nagoya-shi, Aichi (JP)

(72) Inventor: Toshiaki Nakagawa, Higashimurayama (JP)

(73) Assignee: KOWA COMPANY, LTD. (JP)

( * ) Notice: Subject to any disclaimer, the term of this patent is extended or adjusted under 35 U.S.C. 154(b) by 0 days.

(21) Appl. No.: 14/761,973

(22) PCT Filed: Jan. 20, 2014

(86) PCT No.: PCT/JP2014/050888
§ 371 (c)(1),
(2) Date: Jul. 20, 2015

(87) PCT Pub. No.: WO2014/112611
PCT Pub. Date: Jul. 24, 2014

(65) Prior Publication Data
US 2015/0325014 A1    Nov. 12, 2015

(30) Foreign Application Priority Data

Jan. 21, 2013  (JP) ................................. 2013-008262

(51) Int. Cl.
*G06T 11/00*   (2006.01)
*A61B 3/12*    (2006.01)
*H04N 1/409*   (2006.01)
(Continued)

(52) U.S. Cl.
CPC ............... *G06T 11/008* (2013.01); *A61B 3/12* (2013.01); *G06T 5/002* (2013.01); *G06T 5/50* (2013.01); *H04N 1/409* (2013.01); *H04N 5/21* (2013.01); *G06T 2207/10004* (2013.01); *G06T 2207/10101* (2013.01); *G06T 2207/20216* (2013.01); *G06T 2207/30041* (2013.01); *H04N 5/357* (2013.01)

(58) Field of Classification Search
None
See application file for complete search history.

(56) References Cited

U.S. PATENT DOCUMENTS

| 5,911,012 A | 6/1999 | Bernard et al. ............... 382/260 |
| 2003/0228067 A1 | 12/2003 | Miyake et al. ............... 382/275 |

(Continued)

FOREIGN PATENT DOCUMENTS

| EP | 2189109 | 5/2010 |
| JP | 9128532 | 5/1997 |

(Continued)

OTHER PUBLICATIONS

International Search Report mailed Apr. 8, 2014 issued in International Appln. No. PCT/JP2014/050888.

(Continued)

*Primary Examiner* — Siamak Harandi
(74) *Attorney, Agent, or Firm* — Adams & Wilks (57) ABSTRACT

An average image producing means 52 produces an average image from all or some of a plurality of images captured at the same location. A noise extracting means 53 extracts a noise pixel on the basis of the result of a comparison between the pixel values of the pixels in the captured images and the pixel values of the pixels at the same position in the average image. An interpolating means 54 interpolates the pixel value of the noise pixel included in the captured images using the pixel values of other pixels to produce a noise-eliminated image.

10 Claims, 8 Drawing Sheets

(51) Int. Cl.
*H04N 5/21* (2006.01)
*G06T 5/00* (2006.01)
*G06T 5/50* (2006.01)
*H04N 5/357* (2011.01)

(56) References Cited

U.S. PATENT DOCUMENTS

| | | | |
|---|---|---|---|
| 2011/0211758 A1 | 9/2011 | Joshi et al. | 382/167 |
| 2011/0234842 A1 | 9/2011 | Ishiga | 348/246 |
| 2011/0274350 A1* | 11/2011 | Hara | G06T 5/20 |
| | | | 382/167 |
| 2012/0314107 A1 | 12/2012 | Kanemitsu et al. | 348/246 |

FOREIGN PATENT DOCUMENTS

| | | |
|---|---|---|
| JP | 2005286689 | 10/2005 |
| JP | 3862613 | 12/2006 |
| JP | 2008131580 | 6/2008 |
| JP | 4535125 | 9/2010 |
| JP | 2011135566 | 7/2011 |
| JP | 2012105063 | 5/2012 |
| JP | 2012253725 | 12/2012 |
| WO | 2006106919 | 10/2006 |
| WO | 2008119480 | 10/2008 |
| WO | 2010007777 | 1/2010 |
| WO | 2011108231 | 9/2011 |
| WO | 2012124516 | 9/2012 |
| WO | 2012222510 | 11/2012 |

OTHER PUBLICATIONS

European Search Report mailed Jul. 22, 2016 issued in Application No. EP 14 74 0744.
B. Sander: "Enhanced optical coherence tomography imaging by multiple scan averaging", British Journal of Ophthalmology, vol. 89, No. 2, Feb. 2005 (Feb. 2005), pp. 207-212 XP055044967, ISSN: 0007-1161, DOI: 10.1136/bjo.2004.045989.
Boyce J M Ed—Institute of Electrical and Electronics Engineers: "Noise Reduction of Image Sequences Using Adaptive Motion Compensated Frame Averaging", Speech Procesing 1. San Francisco, Mar. 23-26, 1992; [Proceedings of the International Conference on Acoustics, Speech and Signal Processing (ICASSP)], New York, IEEE, US, vol. 3, Mar. 23, 1992 (Mar. 23, 1992), pp. 461-464, XP000378968, DOI: 10.1109/ICASSP.1992.226176 ISBN: 978-0-7803-0532-8.

\* cited by examiner

IMAGE PROCESSING DEVICE, IMAGE PROCESSING METHOD, IMAGE PROCESSING PROGRAM, AND RECORDING MEDIUM STORING SAID PROGRAM FOR PRODUCING NOISE-ELIMINATED IMAGE

TECHNICAL FIELD

The present invention relates to an image processing device for processing an image obtained by photographing the form of an object such as an eye to be examined, an image processing method, an image processing program, and a recording medium storing the program.

BACKGROUND ART

Various methods for eliminating noise from images obtained by an imaging device such as a CCD have been proposed. For example, Patent Document 1 discloses a method in which, on the basis of the pixel value of a selected pixel and the pixel value of a pixel of interest, a new pixel value of the pixel of interest is determined, and the pixel value of the pixel of interest is replaced with the new pixel value to generate new image data, thereby eliminating noise from image data including low-frequency noise.

Patent Document 2 discloses a method in which a substantially simultaneously acquired image in a full pixel read-out mode and an image in a pixel summation read-out mode are separated respectively into luminance components and color difference components for adaptive synthetic processing.

Patent Document 3 discloses a method in which, for a pixel to be corrected, the highest value is calculated from among pixel values of a plurality of surrounding same-color pixels having the same color component as the pixel to be corrected, and among pixel values of a plurality of surrounding different-color pixels having a color component different from that of the pixel to be corrected, the plurality of surrounding different-color pixels being closer to the pixel to be corrected than are the plurality of surrounding same-color pixels, and, when the pixel value of the pixel to be corrected is higher than the calculated highest value, the pixel value of the pixel to be corrected is replaced with the calculated highest value to correct a white defect.

Patent Document 4 discloses an image processing device for eliminating noise from a moving image, the device comprising: a contrast calculation unit for calculating a contrast value for a target pixel in a basis image; a motion vector calculation unit for calculating a motion vector between the basis image and the reference image, the motion vector calculation unit using the contrast value to modify the method for calculating the motion vector; a motion compensation unit for compensating for motion of the reference image with respect to the basis image on the basis of the motion vector calculated by the motion vector calculation unit; and a weighted addition unit for performing weighted addition of the basis image and the reference image subjected to motion compensation for each target pixel.

Patent Document 5 discloses an image processing device in which an inputted image and a reference image are added to eliminate noise in the inputted image.

Patent Document 6 discloses an image processing method for eliminating noise included in an image, the method comprising extracting a high-frequency component from an image, extracting a noise component from the extracted high-frequency component using non-linear conversion, subtracting the extracted noise component from the image, again extracting the high-frequency component from the image from which the noise component was subtracted, extracting a correction component using non-linear conversion from the high-frequency component that was extracted again, and adding the extracted correction component to the image from which the noise component was subtracted.

PRIOR ART DOCUMENTS

Patent Documents

Patent Document 1: Japanese Patent No. 3862613
Patent Document 2: Japanese Patent Laid-open Publication No. 2008-131580
Patent Document 3: Japanese Patent Laid-open Publication No. 2011-135566
Patent Document 4: Japanese Patent Laid-open Publication No. 2012-222510
Patent Document 5: Domestic Re-publication of PCT International Application No. 2010-007777
Patent Document 6: Japanese Patent No. 4535125

SUMMARY OF INVENTION

Problems to be Solved

The prior art described above presents a problem in that, if the signal and noise characteristics are not clearly separated, the effect of noise elimination is diminished and the signal intensity may be reduced. Therefore, it is an object of the present invention to provide an image processing device for eliminating noise from an image while maintaining signal intensity, an image processing method, an image processing program, and a recording medium storing the program.

Means for Solving the Problems

An image processing device of the present invention that solves the problems described above, comprises:
average image producing means for producing an average image from all or some of a plurality of images captured at the same location;
noise extracting means for extracting a noise pixel on the basis of the result of a comparison between the pixel values of the pixels in the captured images and the pixel values of the corresponding pixels in the average image; and
interpolating means for interpolating the pixel value of the noise pixel included in the captured images using the pixel values of other pixels to produce a noise-eliminated image.

Effect of the Invention

According to the present invention, a noise pixel is extracted on the basis of the difference in pixel values between a captured image and an average image. It is therefore possible to eliminate noise from an image while maintaining signal intensity.

MODE OF CARRYING OUT THE INVENTION

An image processing device according to the present invention will be described in detail below on the basis of embodiments and with reference to the attached drawings. Description will be given of an example in which a tomographic image (one example of a captured image) of the fundus of an eye to be examined is acquired by an ophthalmologic examination apparatus and noise is eliminated from the tomographic image; however, the present invention can also be applied to cases in which other objects are captured using other types of apparatuses.

Embodiment 1

Figure 1:
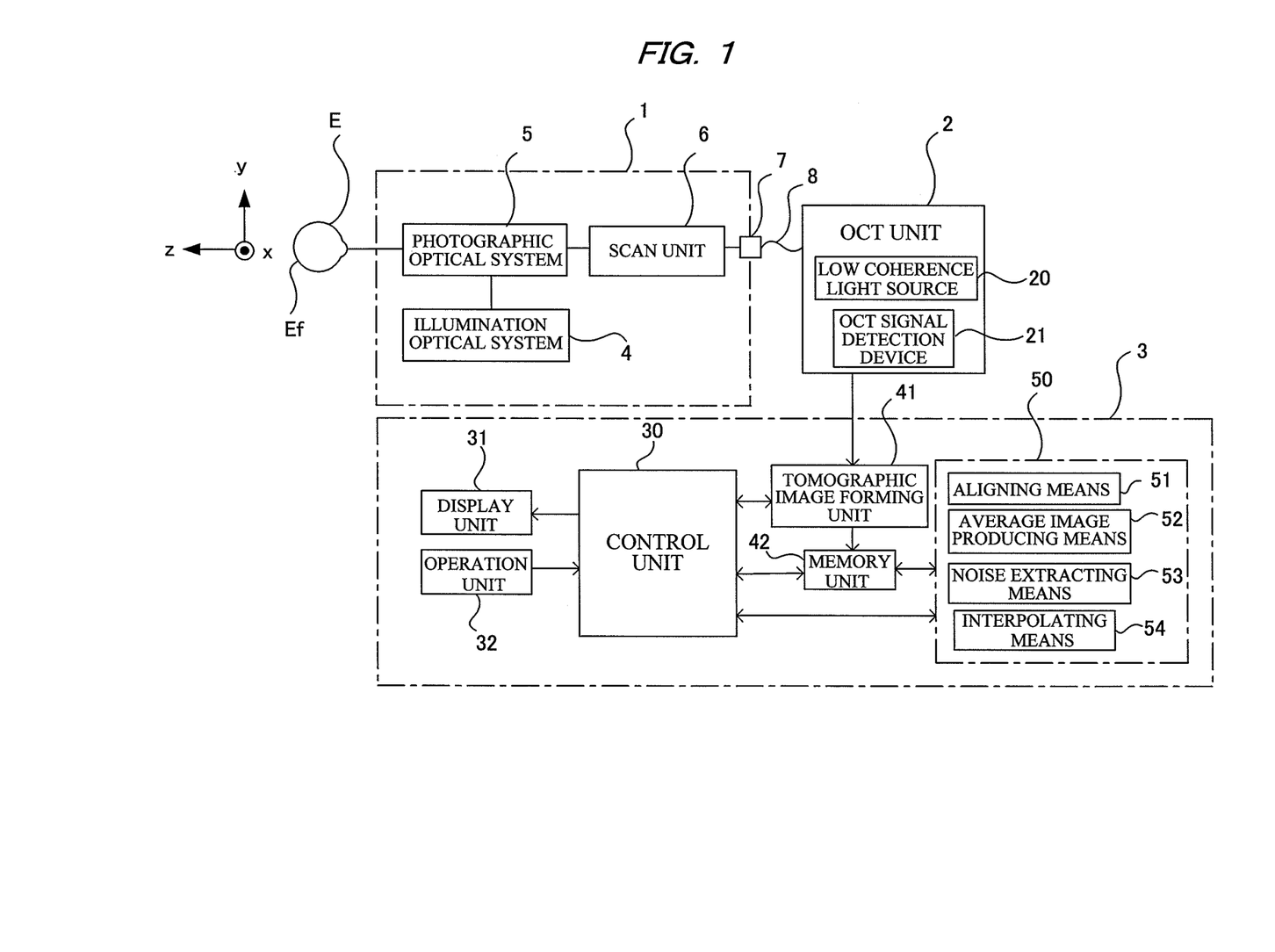
FIG. 1 is a block diagram showing the entirety of a system for acquiring a tomographic image of the fundus of an eye to be examined and processing the image.

FIG. 1 is a block diagram showing the entirety of a system for acquiring a tomographic image of the fundus of an eye to be examined and processing the image. Reference numeral 1 indicates a fundus camera unit 1 for observing and capturing an image of the fundus (retina) Ef of an eye E to be examined. The fundus camera unit 1 includes an illumination optical system 4, a photographic optical system 5, and a scan unit 6.

The illumination optical system 4 includes an observation light source such as a halogen lamp and a photographing light source such as a xenon lamp. The light from these light sources is guided to the fundus Ef via the illumination optical system 4 to illuminate the fundus. The photographic optical system 5 includes optical elements such as an objective lens and a photographic lens, and an imaging device such as a CCD. The photographic optical system 5 guides photographing light reflected by the fundus Ef along a photographing optical path to the imaging device to capture an image of the fundus Ef. The photographic optical system 5 also guides below described signal light from the OCT unit 2 to the fundus Ef and light reflected therefrom to the OCT unit 2. The scan unit 6 includes mechanisms such as galvanometer mirrors for scanning the signal light from the OCT unit 2 in the X direction and Y direction as shown in FIG. 1.

The fundus camera unit 1 is optically connected via a connector 7 and a connecting wire 8 to the OCT unit 2 for capturing a tomographic image of the fundus Ef.

The OCT unit 2 may be not only of a Fourier domain type, but also of a time domain or a swept-source type; however, the OCT unit 2 will use a well-known Fourier domain type. In this case, a low coherence light source 20 emits light having a wavelength of 700-1100 nm. The light from the low coherence light source 20 is divided into reference light and signal light, and the reference light advances on a reference optical path and is reflected by a reference mirror. On the other hand, the signal light is guided to the fundus camera unit 1 via the connecting wire 8 and the connector 7, and is scanned on the fundus Ef in the X and Y directions by the scan unit 6. The signal light reflected by the fundus Ef and returned to the OCT unit 2 is superimposed on the reference light reflected by the reference mirror to produce interference light. The interference light is analyzed in spectrum in an OCT signal detection device 21 to generate an OCT signal that indicates information about the depth direction (Z direction) of the fundus.

An image processing device 3 is configured from, e.g., a microcomputer built in the fundus camera unit 1, or a personal computer connected to the fundus camera unit 1. The image processing device 3 is provided with a control unit 30 configured from CPU, RAM, ROM, and the like. The control unit 30 controls all image processing by executing an image processing program.

A display unit 31 is configured from, e.g., a display device such as an LCD, and displays an image produced or processed by the image processing device 3 and ancillary information such as information relating to a subject.

An operation unit 32 has, e.g., a mouse, keyboard, operation panel and the like, and is used by an operator to give commands to the image processing device 3.

A tomographic image forming unit 41 is implemented by a dedicated electronic circuit for executing a well-known analysis method such as a Fourier domain method (spectral domain method) or by the image processing program executed by the CPU described above, and forms a tomographic image of the fundus Ef on the basis of the OCT signal detected by the OCT signal detection device 21. The tomographic image formed by the tomographic image forming unit 41 is stored in a memory unit 42 configured from, e.g., a semiconductor memory, hard disk device, or the like. The memory unit 42 also stores the image processing program described above.

An image processing unit 50 performs a computation process on the tomographic image (captured image) formed by the tomographic image forming unit 41 and eliminates noise included in the tomographic image. The image processing unit 50 is configured from aligning means 51 for aligning other captured images with a reference image, average image producing means 52 for producing an average image from all or some of the captured images, noise extracting means 53 for extracting a noise pixel on the basis of the result of a comparison between the pixel values of the pixels in the captured images and the pixel values of the corresponding pixels in the average image, and interpolating means 54 for interpolating the pixel value of the noise pixel with the pixel values of other pixels to produce a noise-eliminated image. The means or image processes in the image processing unit 50 are implemented by use of the dedicated electronic circuit, or by executing the image processing program by the control unit 30.

Figure 2:
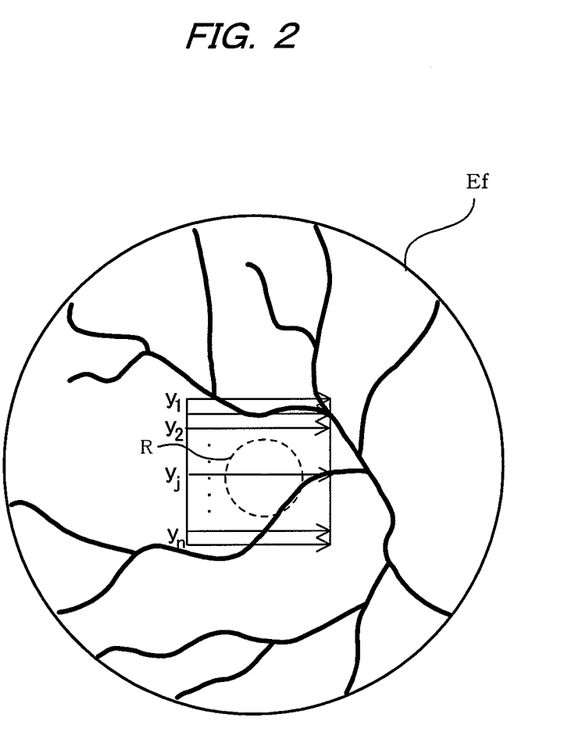
FIG. 2 is an illustrative view showing a state in which a macular area of the fundus is scanned using signal light.
Figure 3:
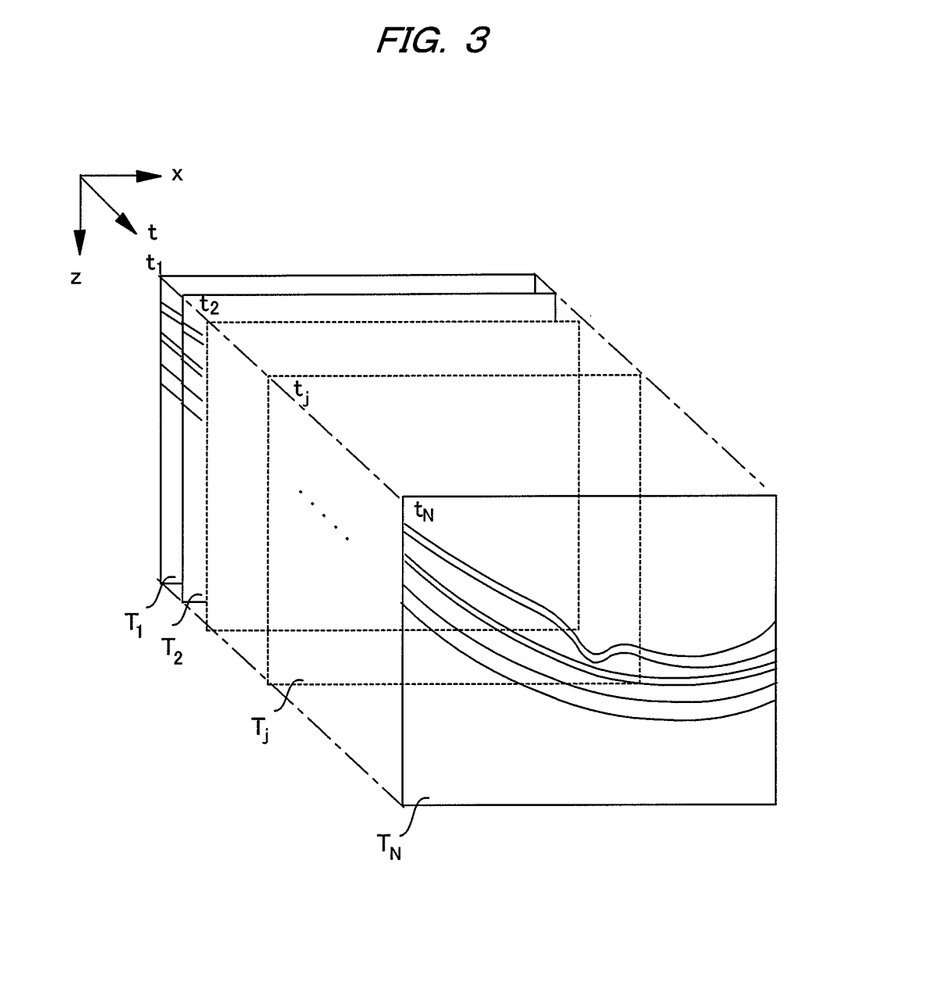
FIG. 3 is an illustrative view showing a state in which a plurality of tomographic images are acquired.

The operation of the image processing device 3 will be described next with reference to the flowchart in FIG. 4. The control unit 30 controls the scan unit 6 to scan the signal light on the fundus Ef at one location in the X-axis direction in FIG. 1. At this time, the tomographic image forming unit 41 forms one tomographic image on the basis of the OCT signal detected by the OCT signal detection device 21. These processes are repeated N times (where N is an integer equal to or greater than 2, e.g., N=100-300). This causes N tomographic images $T_i$ (with i being 1 through N) (written as $T_i$ below) of the fundus Ef at the same location at different times $t_1$-$t_N$ to be produced (step S1). FIG. 3 is an example of a plurality of tomographic images along scanning lines $y_j$ in a region R in which a retinal macular region as shown in FIG. 2 is present. Structures constituting the fundus appear in layers in each of the tomographic images $T_i$. These images are obtained by photographing the same location (by selecting the position of the scan line $y_j$ in FIG. 2); however, positional shifts may occur in the X-axis direction and Z-axis direction due to involuntary eye movement during fixation. The thus produced tomographic images $T_i$ usually have low signal intensity and include a large amount of noise.

The aligning means 51 performs a process in which each of the tomographic images $T_i$ is aligned with a reference image (step S2). Specifically, a reference image serving as an alignment reference is first selected or produced. The reference image may be any tomographic image, e.g., the first tomographic image $T_1$, or $T_i$ that is displayed on the display unit 31 and selected by an operator. Alternatively, an average image of the tomographic images $T_i$, the tomographic image most similar to this average image, or an average image of a plurality of tomographic images selected by an operator may be used as the reference image.

Figure 5:
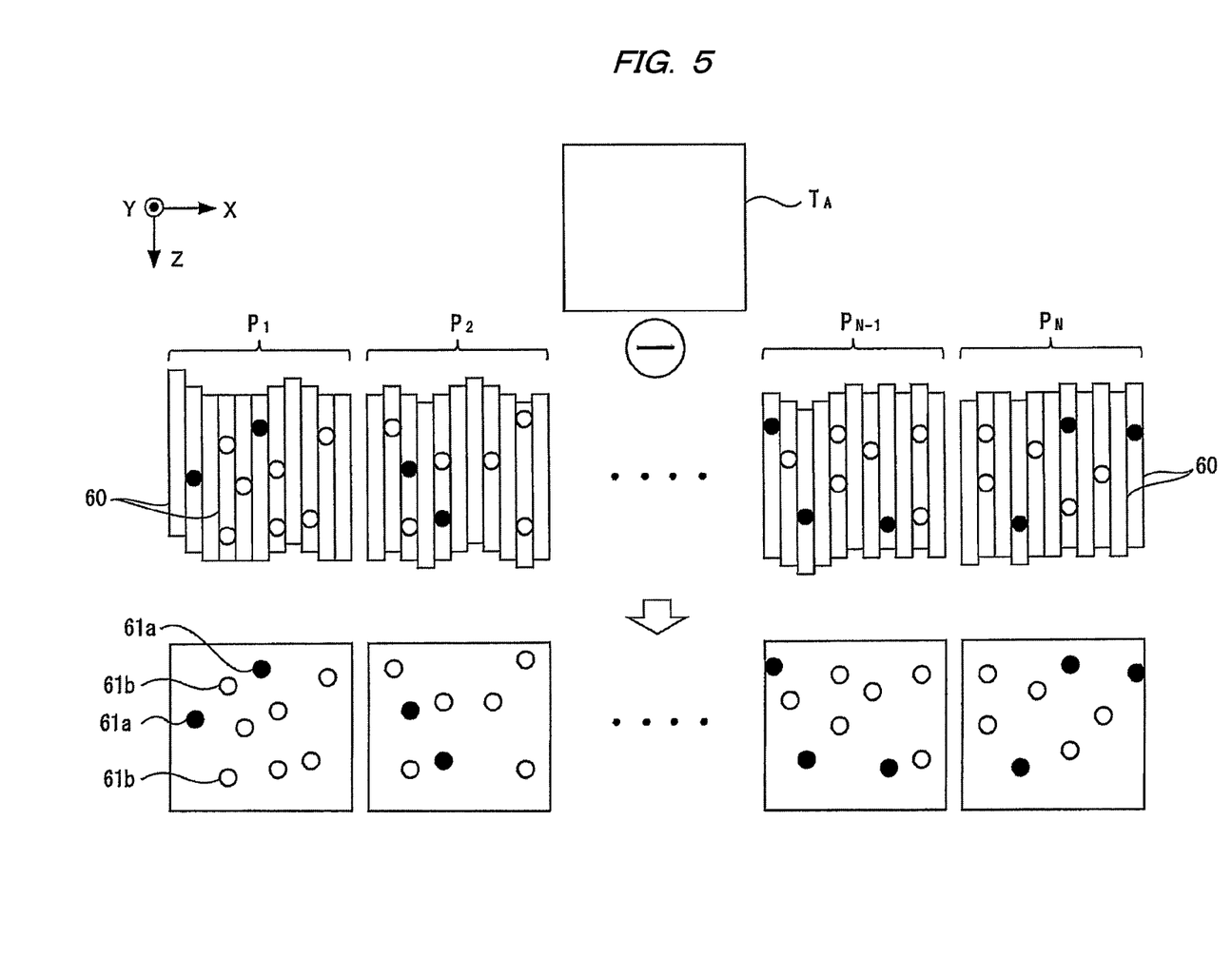
FIG. 5 is a schematic view illustrating an aligning process and a process for extracting noise pixels.

Next, as shown in FIG. 5, each of the tomographic images $T_i$ is divided into strip regions 60 such that each of the strip regions 60 is k pixels wide in the X direction (where, e.g., k=1). Next, local regions are set so as to be about 20 k pixels wide in the X direction and so as to have the same length in the Z direction as the strip region 60, and the degree of similarity relative to the corresponding local region of the reference image is calculated for each of the strip regions on the basis of the set local regions to calculate the amount of shifts in the X direction and Z direction. Each of the strip regions is then moved in the X direction and Z direction by the calculated amount of shifts, thereby performing the aligning process to produce an aligned tomographic image $P_i$ as shown in the middle section of FIG. 5. In FIG. 5, the positions of the strip regions 60 of the aligned tomographic image Pi are irregular in the Z direction (vertical direction). This schematically represents the amount of shifts in the Z direction. However, the amount of shift in the X direction is not shown because it is difficult to represent. The value of k can be changed in accordance with expected noise size, image magnification, and the like. The degree of similarity can be calculated using, e.g., formula 1 below.

$$r = \frac{\sum_{k=1}^{n}\{T_A(k)-\overline{T_A}\}\{T_i(k)-\overline{T_i}\}}{\sqrt{\sum_{k=1}^{n}\{T_A(k)-\overline{T_A}\}^2}\sqrt{\sum_{k=1}^{n}\{T_i(k)-\overline{Ti}\}^2}}$$ Formula 1

In Formula 1, T(k) represents a set of pixel values (the number of pixels n), and T (with a horizontal line above) represents the average of the pixel values.

Alignment can be performed by a variety of methods other than the method described above. For example, a method may be used in which alignment is performed on the entirety of the tomographic images without dividing the tomographic images into strip regions, or a method may be used in which parts of the tomographic images are extracted as characteristic, regions, and alignment is performed on the basis of the degree of similarity of these characteristic regions. Depending on the properties of the photographic object, the aligning process may be omitted.

The average image producing means 52 adds together the pixel values of the aligned tomographic images $P_1$-$P_N$ for each of the pixels, and divides the resulting sum by the number of images N. This determines the pixel value of each of the pixels and produces an averaged image $T_A$ (step S3). The averaged image may be produced from some of the tomographic images $P_i$, rather than being produced from all of the aligned tomographic images $P_i$ as described above. Alternatively, the pixel values of the averaged image may be determined using the median value or the most frequently appearing value of the pixel values of the tomographic images, rather than using the arithmetic mean of the pixel values.

The noise extracting means 53 calculates the difference between the pixel value of each of the pixels in the aligned tomographic image $P_i$ and the pixel value of the pixel in the averaged image $T_A$ that is located at the same position as the pixel in the aligned tomographic image $P_i$, and, when the absolute value of this difference is greater than a prescribed threshold, determines that the pixel is a noise pixel (step S4). The threshold may be incrementally varied in accordance with the pixel values of the averaged image $T_A$, rather than using a single value.

The comparison between the pixel value of each of the pixels in the tomographic image $T_i$ and the pixel value of the pixel in the averaged image $T_A$ that is located at the same position as the pixel in the tomographic image $T_i$ may be performed using a ratio, and a pixel may be determined to be a noise pixel when the ratio deviates from a prescribed range.

In the case of tomographic images by OCT as in the present embodiment, noise pixels may include pixels having low pixel values due to the structure of the fundus, as indicated by the black circles (reference symbol 61a) in FIG. 5, and pixels having high pixel values (shot noise) due to the imaging device, as indicated by the white circles (reference symbol 61b) in FIG. 5. The noise extracting means 53 extracts the pixels determined to include noise for each of the tomographic images $P_i$, as shown in the lower section of FIG. 5, and stores in the memory unit 42 information specifying these pixels, e.g., the X and Z coordinates of the noise pixels.

Figure 6:
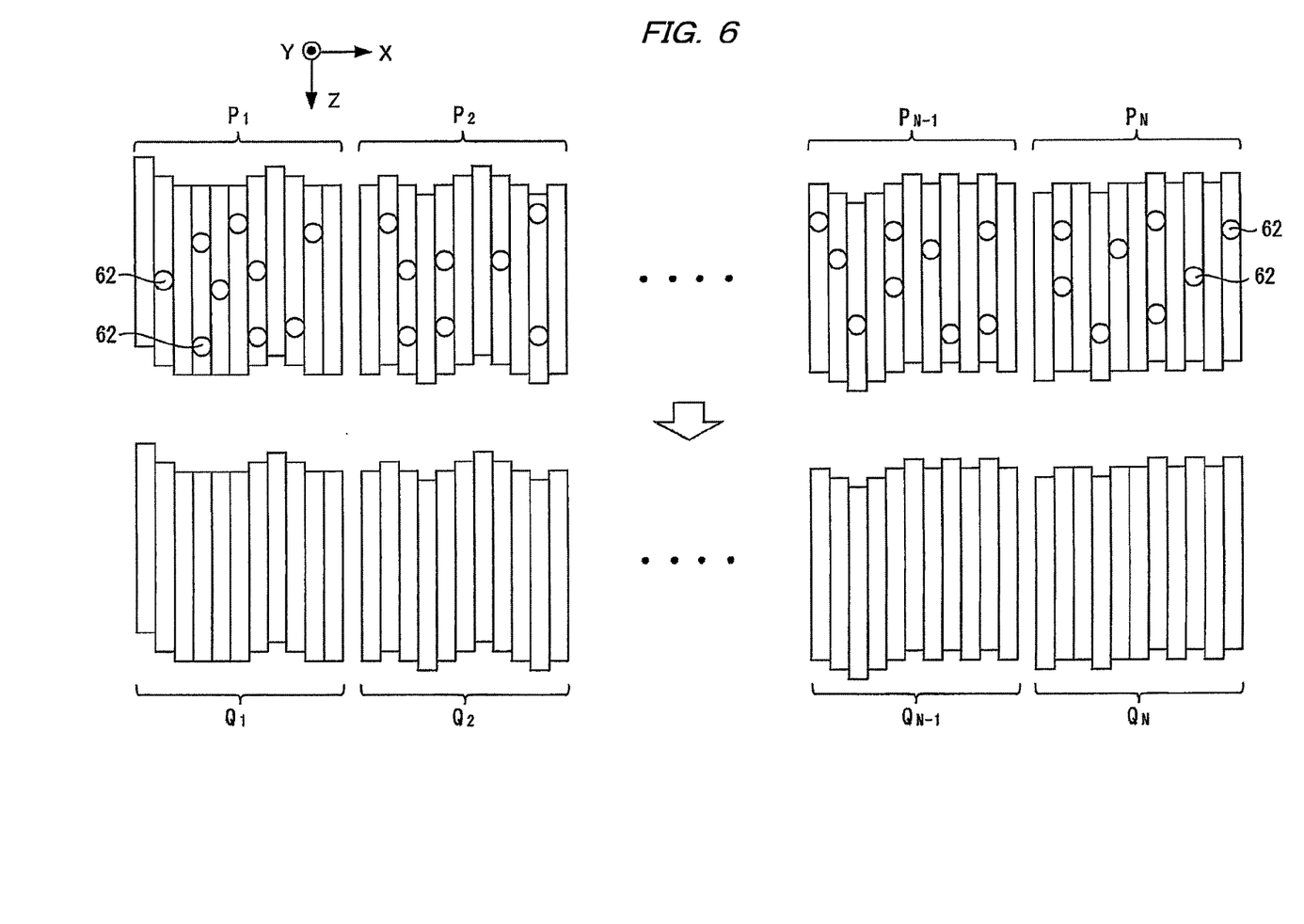
FIG. 6 is a schematic view illustrating a noise-pixel elimination and an interpolation process.

The interpolating means 54 deletes the pixels determined in step S4 to include noise as shown by reference symbol 62 in the upper section of FIG. 6 (e.g., sets the pixel values thereof to 0). The pixel values of the deleted pixels 62 are then interpolated on the basis of, e.g., the pixel values of pixels adjacent to the deleted pixels, or the pixel values of pixels within a certain distance from the deleted pixels, and tomographic images $Q_1$-$Q_N$ from which noise was eliminated (as an example of noise-eliminated images) are produced and stored in the memory unit 42 (step S5). A variety of well-known methods other than that described above can be used as the method for interpolation.

The tomographic images $Q_1$-$Q_N$ stored in the memory unit 42 from which noise was eliminated are displayed on the display unit 31 either one at a time or with a plurality of images lined up in a single screen image by the control unit 30 on the basis of commands given by an operator via the operation unit 32.

According to the image processing device 3 of the present embodiment, noise pixels are extracted on the basis of the result of a comparison between the pixel values of each of the aligned tomographic images $P_i$ and the averaged image $T_A$, and an interpolating process is performed for the noise pixels. It is therefore possible to eliminate noise while maintaining signal intensity, even when the signal intensity of the tomographic images $T_i$ is low.

Because extraction of noise pixels and interpolation of noise pixels are each performed for all of the tomographic images $T_i$, a plurality of (N) distinct tomographic images from which noise was eliminated can be obtained.

Embodiment 2

Figure 7:
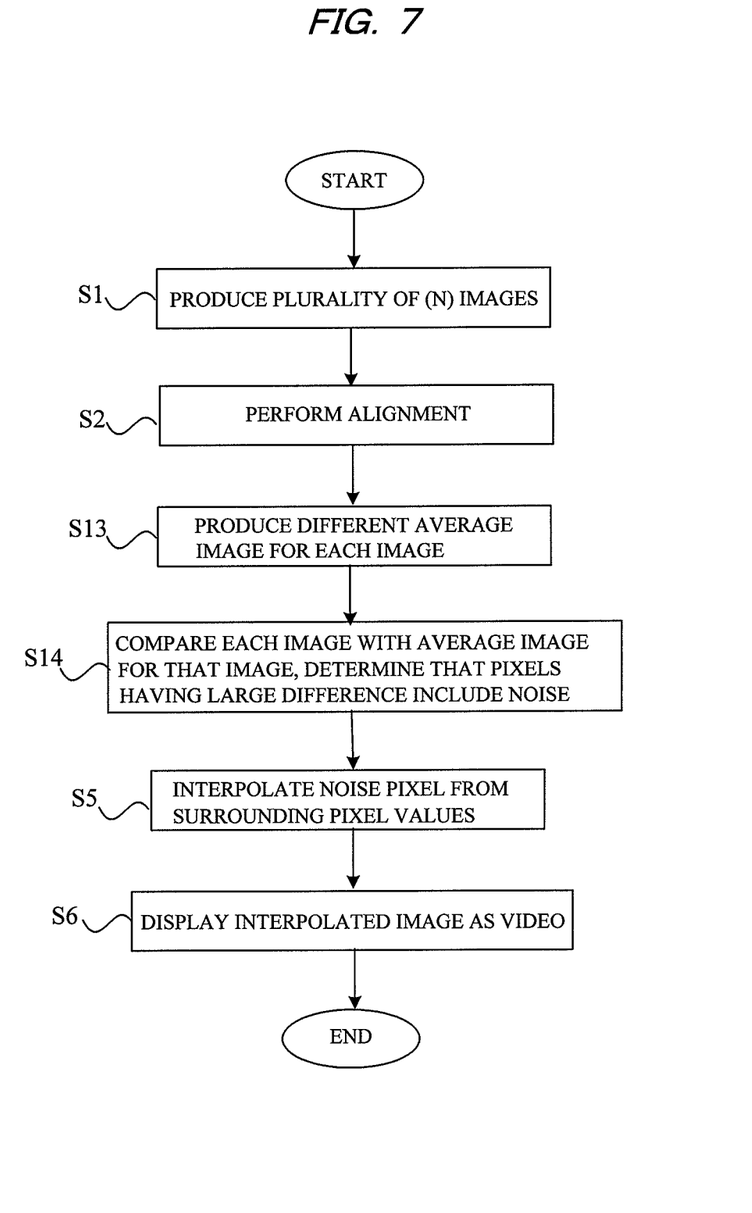
FIG. 7 is a flowchart showing the procedure for a noise elimination process.

A second embodiment of the present invention will be described next. The configuration of the device in the second embodiment is the same as that in the first embodiment shown in FIG. 1. The operation of the device is also essentially the same as in the first embodiment; therefore, portions different from the first embodiment will be described with reference to the flowchart in FIG. 7 and the schematic view in FIG. 8.

The tomographic image forming unit 41 forms N tomographic images $R_1$-$R_N$ of the same location on the fundus Ef of an eye E to be examined, and the aligning means 51 aligns each of the tomographic images $R_i$. These processes are the same as in the first embodiment (steps S1 and S2). Depending on the photographed object, the aligning process can be omitted, the same as in the first embodiment. Noise pixels are included in the produced tomographic images $R_i$, as indicated by the black circles (reference numeral 63) in FIG. 8.

Figure 8:
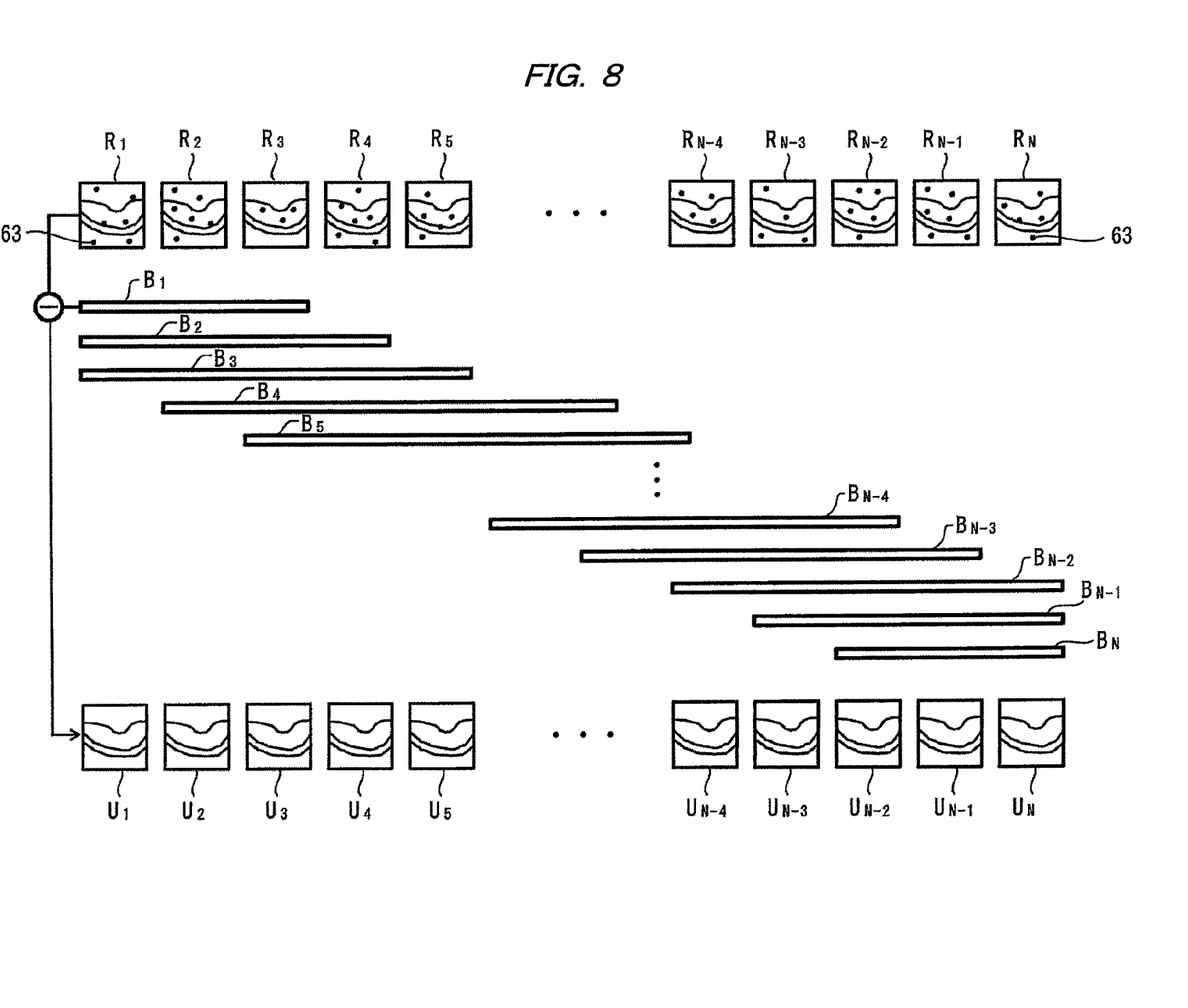
FIG. 8 is a schematic view illustrating a process for generating video.

The average image producing means 52 uses tomographic images having a difference in photographing time less than a prescribed threshold relative to the tomographic images $R_i$ to produce a different individual average image $B_i$ for the tomographic images $R_i$ (step S13). Specifically, for example, for the constant time required for a single scan in the X direction, the individual average image $B_i$ for the tomographic images $R_i$ is produced using the same method as in step S3 in FIG. 4 from the tomographic image $R_i$ and M tomographic images preceding and following same (where M is an integer equal to or greater than 1 and less than N), i.e., from the 2M+1 tomographic images $T_{i-M}$-$T_{i+M}$. FIG. 8 shows an example in which individual average images $B_i$ are produced from, with M being 2, in principle five tomographic images. The thick lines indicating the individual average images $B_i$ show the range of tomographic images used in the production of the individual average images $B_i$.

When the number of tomographic images preceding or following a tomographic image Ri is less than M as with $R_1$, $R_2$, $R_{N-1}$ and $R_N$ in FIG. 8, the average image forming means 52 forms an individual average image $B_i$ using fewer than 2M+1 tomographic images without compensating for the insufficiency. For example, because there are no tomographic images preceding the tomographic image $R_1$, an individual average image is produced using only three tomographic images $R_1$, $R_2$, and $R_3$. This is because, rather than increasing the number of tomographic images used in the production of the individual averaged images to improve the sharpness thereof, priority is given to avoid an increase in photographing time difference between the tomographic image $R_i$ of interest and the last (first) tomographic image used in the production of an individual average image. For example, when an averaged image for the tomographic image $R_1$ is produced using the tomographic images $R_1$-$R_5$ to compensate for the insufficiency, the difference in time between the tomographic image $R_1$ and the very last tomographic image $R_5$ may increase, and actually occurring changes in the images such as those in the shape of a blood vessel due to pulsation may be determined to be noise and be eliminated.

Figure 4:
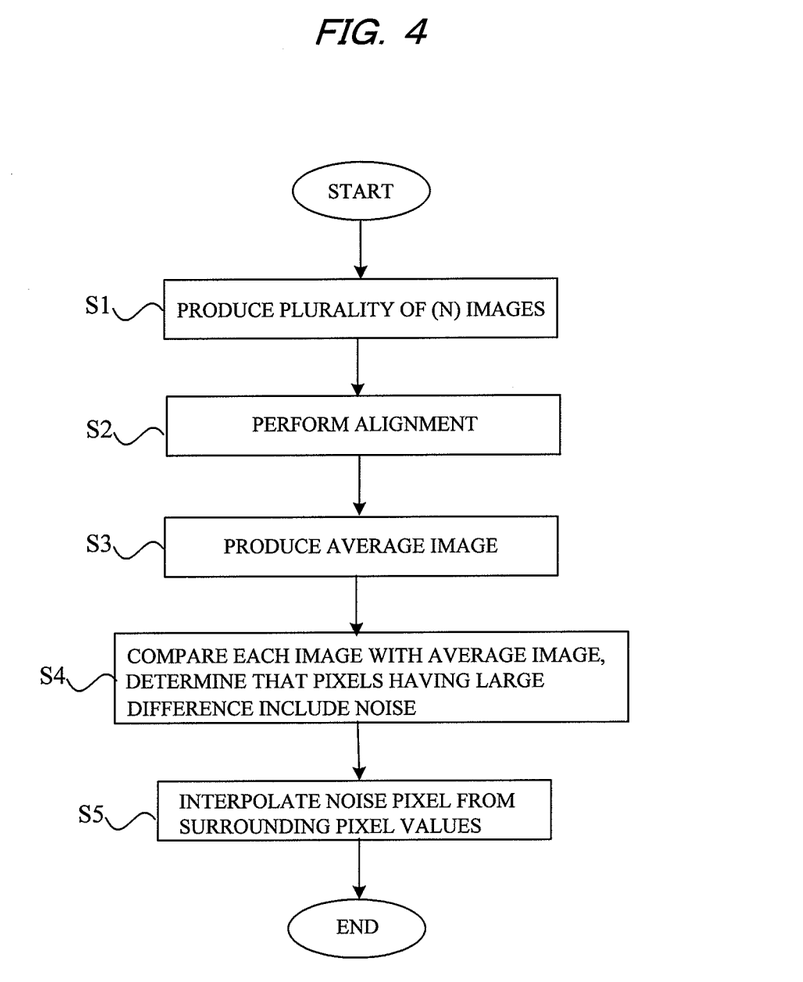
FIG. 4 is a flowchart showing the procedure for a noise elimination process.

The noise extracting means 53 performs a subtraction process on the pixel values in each of the tomographic images $R_i$ and the individual average images $B_i$, and extracts noise pixels using the same method as in step S4 in FIG. 4 (step S14).

The interpolating means 54 interpolates the noise pixels, produces tomographic images $U_1$-$U_N$ from which noise was eliminated, and stores these tomographic images $U_1$-$U_N$ in the memory unit 42. This process is the same as that used in the first embodiment (step S5).

The control unit 30 causes the noise-eliminated tomographic images $U_1$-$U_N$ from the memory unit 42 to be displayed as video on the display unit 31 (step S6). Specifically, the tomographic images $U_i$ are taken as single frames of video, and the tomographic images $U_1$-$U_N$ are displayed in sequence at appropriate time intervals. Alternatively, a file in video format may be generated from the tomographic images $U_1$-$U_N$ and played back.

In the present embodiment, the tomographic images $U_1$-$U_N$ from which noise was eliminated are all stored in the memory unit 42, and then video is displayed. However, if the processing power of the image processing device 3 is great enough, it is possible to perform these processes in real time. Specifically, when the time required for producing a single tomographic image and performing the series of processes on this tomographic image is shorter than the time for performing a single scan in the X direction, the processes in steps S2-S6 in FIG. 7 may be performed in parallel with the tomographic image capturing.

Also in the second embodiment, the tomographic images $U_i$ from which noise was eliminated may be displayed on the display unit 31 as still images.

According to the image processing device 3 of the second embodiment, an average image serving as the reference for the process of extracting noise pixels is produced for every individual tomographic image solely from the tomographic images having a small photographing time difference relative to the respective tomographic image. Therefore, it is possible to avoid a situation in which a change such as pulsation of a blood vessel that actually occurs in a photographed object is determined to be noise and is eliminated. Additionally, the noise-eliminated tomographic images $U_i$ are displayed as video. This allows an operator to observe movements in blood vessels, thus helping in making a diagnosis.

KEY TO THE SYMBOLS

1 Fundus camera unit
2 OCT unit
3 Image processing device
4 Illumination optical system
5 Photographic optical system
6 Scan unit
7 Connector
8 Connecting wire
20 Low coherence light source
21 OCT signal detection device
30 Control unit
31 Display unit
32 Operation unit
41 Tomographic image forming unit
42 Memory unit
50 Image processing unit
51 Aligning means
52 Average image producing means
53 Noise extracting means
54 Interpolating means
60 Strip region 61a, 61b, 63 Noise pixel
62 Deleted noise pixel
E Eye to be examined
Ef Fundus
$T_i$, $R_i$ Tomographic image
$P_i$ Tomographic image after aligning process
$Q_i$, $U_i$ Tomographic image from which noise was eliminated

The invention claimed is:

1. An image processing device comprising:
average image producing means for producing an average image from all or some of a plurality of images captured at the same location;
noise extracting means for extracting a noise pixel on the basis of the result of a comparison between pixel values of pixels in the captured images and pixel values of pixels at the same position in the average image; and
interpolating means for interpolating the pixel value of the noise pixel included in the captured images using the pixel values of other pixels to produce a noise-eliminated image.

2. An image processing device according to claim 1, further comprising aligning means for aligning the captured images on the basis of a reference image selected or generated from a plurality of the captured images,
wherein the average image producing means produces the average image from the aligned captured images;
the noise extracting means extracts the noise pixel on the basis of the result of a comparison between the pixel values of the pixels in the aligned captured images and the pixel values of the pixels at the same position in the average image that is produced from the aligned captured images; and
the interpolating means interpolates the pixel value of the extracted noise pixel using the pixel values of pixels adjacent to the extracted noise pixel to produce a noise-eliminated image.

3. An image processing device according to claim 1, wherein the noise extracting means calculates a difference between the pixel values of the pixels in the captured images and the pixel values of the corresponding pixels in the average image and extracts as a noise pixel a pixel for which the absolute value of the difference is greater than a threshold.

4. An image processing device according to claim 1, wherein the average image producing means produces a different individual average image for each of the captured images, and the noise extracting means extracts the noise pixel on the basis of the result of a comparison between the pixel values of the pixels in the captured images and the pixel values of the corresponding pixels in the individual average image.

5. An image processing device according to claim 4, wherein the average image producing means produces the individual average image from captured images in which the difference in photographing time in the captured image is less than a threshold.

6. An image processing device according to claim 4, wherein the average image producing means produces the individual average image from a captured image and a prescribed number of other captured images closely back and forth in photographing time in the captured image.

7. An image processing device according to claim 1, comprising a control unit that causes the noise-eliminated images to be displayed as video.

8. An image processing method comprising:
producing an average image from all or some of a plurality of images captured at the same location;
extracting a noise pixel on the basis of the result of a comparison between pixel values of pixels in the captured images and pixel values of pixels at the same position in the average image; and
interpolating the pixel value of the noise pixel included in the captured images using the pixel values of other pixels to produce a noise-eliminated image.

9. An image processing program stored on a non-transitory medium executed by a computer comprising:
an average image producing process for producing an average image from all or some of a plurality of images captured at the same location;
a noise extracting process for extracting a noise pixel on the basis of the result of a comparison between pixel values of pixels in the captured images and pixel values of pixels at the same position in the average image; and
an interpolating process for interpolating the pixel value of the noise pixel included in the captured images using the pixel values of other pixels to produce a noise-eliminated image.

10. A non-transitory computer-readable recording medium in which the image processing program of claim 9 is stored.

* * * * *